(12) United States Patent
Woll

(10) Patent No.: US 10,153,215 B2
(45) Date of Patent: Dec. 11, 2018

(54) OVEN ENCLOSURE FOR OPTICAL COMPONENTS WITH INTEGRATED PURGE GAS PRE-HEATER

(71) Applicant: KLA-Tencor Corporation, Milpitas, CA (US)

(72) Inventor: Dirk Woll, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 94 days.

(21) Appl. No.: 15/358,507

(22) Filed: Nov. 22, 2016

(65) Prior Publication Data

US 2018/0040518 A1 Feb. 8, 2018

Related U.S. Application Data (60) Provisional application No. 62/371,046, filed on Aug. 4, 2016.

(51) Int. Cl.
| | |
|---|---|
| *G02F 2/02* | (2006.01) |
| *H01L 21/66* | (2006.01) |
| *F27D 21/02* | (2006.01) |
| *G01N 21/95* | (2006.01) |
| *G03F 1/84* | (2012.01) |
| *H01L 21/67* | (2006.01) |
| *G03F 7/20* | (2006.01) |

(52) U.S. Cl.
CPC ............. *H01L 22/12* (2013.01); *F27D 21/02* (2013.01); *G01N 21/9501* (2013.01); *G03F 1/84* (2013.01); *G03F 7/7065* (2013.01); *H01L 21/67288* (2013.01)

(58) Field of Classification Search
None
See application file for complete search history.

(56) References Cited

U.S. PATENT DOCUMENTS

| | | | |
|---|---|---|---|
| 3,858,056 A * | 12/1974 | Melamed | G02F 1/39 250/214 DC |
| 4,686,685 A | 8/1987 | Hoag | |
| 4,914,276 A * | 4/1990 | Blair | C30B 31/12 118/725 |
| 4,968,121 A | 11/1990 | Bruesselbach et al. | |
| (Continued) | | | |

FOREIGN PATENT DOCUMENTS

CN 203900744 U 10/2014

OTHER PUBLICATIONS

ISA/KR, International Search Report for PCT/US2017/044968 dated Nov. 15, 2017.

(Continued)

*Primary Examiner* — Rhonda Peace
(74) *Attorney, Agent, or Firm* — Hodgson Russ LLP (57) ABSTRACT

A cartridge in an oven enclosure includes a pre-heating feature for an incoming purge gas before the purge gas enters the space around an optical component, such as a nonlinear optical crystal, in an oven cell. The incoming purge gas can be pre-heated as it travels along a gas pathway around a cartridge. The cartridge can include a heater. The oven enclosure can have two windows positioned such that a laser beam can enter through one of the windows, pass through the optical component, and exit through another of the windows. A second harmonic beam can be generated with the optical component.

13 Claims, 6 Drawing Sheets

(56) References Cited

U.S. PATENT DOCUMENTS

| | | | |
|---|---|---|---|
| 5,935,467 A * | 8/1999 | Unternahrer | G02F 1/3501 |
| | | | 219/385 |
| 5,948,300 A | 9/1999 | Gero et al. | |
| 6,198,075 B1 * | 3/2001 | Moffat | C30B 31/10 |
| | | | 118/724 |
| 6,414,784 B1 * | 7/2002 | Oosako | G02F 1/3501 |
| | | | 359/326 |
| 6,664,511 B2 | 12/2003 | Crafts et al. | |
| 6,785,319 B1 | 8/2004 | Ariga et al. | |
| 7,138,640 B1 | 11/2006 | Delgado et al. | |
| 7,420,681 B1 | 9/2008 | Wang et al. | |
| 8,298,335 B2 | 10/2012 | Armstrong | |
| 9,075,026 B2 * | 7/2015 | Urano | G01N 21/9501 |
| 9,097,683 B2 | 8/2015 | Dribinski et al. | |
| 9,250,178 B2 | 2/2016 | Chuang et al. | |
| 2002/0153360 A1 | 10/2002 | Yamazaki et al. | |
| 2004/0037339 A1 | 2/2004 | Watson et al. | |
| 2013/0314710 A1 * | 11/2013 | Levy | G01N 21/211 |
| | | | 356/402 |
| 2015/0075430 A1 | 3/2015 | Shah et al. | |
| 2016/0169815 A1 * | 6/2016 | Chuang | C30B 29/10 |
| | | | 356/237.2 |
| 2018/0040518 A1 * | 2/2018 | Woll | H01L 22/12 |

OTHER PUBLICATIONS

Yariv, Optical Second Harmonic Generation, Quantum Electronics, Wiley, Second Edition, Section 16.5, pp. 421-428 1975.
Yariv, Optical Second-Harmonic Generation, Quantum Electronics, Wiley, Third Edition, Section 16.5, pp. 392-398 1989.

* cited by examiner

OVEN ENCLOSURE FOR OPTICAL COMPONENTS WITH INTEGRATED PURGE GAS PRE-HEATER

CROSS-REFERENCE TO RELATED APPLICATIONS

This application claims priority to the provisional patent application filed Aug. 4, 2016 and assigned U.S. application Ser. No. 62/371,046, the disclosure of which is hereby incorporated by reference.

FIELD OF THE DISCLOSURE

This disclosure relates to optical components.

BACKGROUND OF THE DISCLOSURE

Inspection processes are used at various steps during semiconductor manufacturing to detect defects on wafers to increase yield. Inspection becomes more important to the successful manufacture of semiconductor devices as the dimensions of semiconductor devices decrease because smaller defects can cause the devices to fail. Semiconductor manufacturers seek improved sensitivity to particles, anomalies, and other defect types, while maintaining overall inspection speed (in wafers per hour) in wafer inspection systems.

The demands of the semiconductor industry for wafer and photomask inspection systems exhibiting high throughput and improvements in resolution are ongoing. Some inspection systems try to achieve higher resolution by illuminating the wafer or reticle using light having shorter wavelengths.

Generating light at wavelengths below 400 nm, and especially below 300 nm, can be challenging. Light sources used for semiconductor inspection require relatively high powers, long lifetimes, and stable performance. Light sources meeting these advanced inspection technique requirements do not exist. The lifetime, power, and stability of current DUV frequency converted lasers is generally limited by the frequency conversion crystals and conversion schemes, especially those exposed to DUV wavelengths like 355 nm, 266 nm, 213 nm, and 193 nm.

In spite of the challenges, advantages may be achieved when illuminating the wafer or reticle with light having wavelengths at or below 400 nm. However, providing suitable lasers for high quality wafer and photomask inspection systems is challenging. Conventional lasers generating light in the deep ultraviolet (DUV) range are typically large, expensive devices with relatively short lifetimes. Semiconductor wafer and photomask inspection systems generally require a laser having a high average power, low peak power, and relatively short wavelength to provide inspection having sufficient throughput and adequate defect signal-to-noise ratio (SNR).

High efficiency can be important for a DUV laser. High efficiency can allow a lower power fundamental laser source that can be more reliable, can be smaller, and can produce less heat. A low power fundamental laser can produce less spectral broadening if a fiber laser is used. Higher efficiency also tends to lead to lower cost and better stability. For these reasons, efficient frequency conversion to the DUV may be sought.

The primary method to provide adequate DUV power entails generating shorter wavelength light from longer wavelength light. This process of changing wavelengths is commonly called frequency conversion. Frequency conversion in this context uses high peak power density light to produce a nonlinear response in an optical crystal. To increase the efficiency of this process, the longer wavelength light may have high average powers, short optical pulses, and may be focused into the optical crystal. The original light is typically called fundamental light.

Relatively few nonlinear crystals are capable of efficient frequency conversion of light to UV/DUV wavelengths. Most crystals that have traditionally been employed have low damage thresholds if not properly prepared and if a tightly controlled operating environment is not maintained. Thus, the crystal has typically been contained within an enclosure to maintain the environment. To frequency convert an infrared laser to DUV, more than one crystal can be employed. When multiple crystals are employed, it can be advantageous to place them all within the enclosure. Crystal alignment complications can result, and it can be difficult to collect and focus light in such an enclosure.

Each successive node of semiconductor manufacturing requires detection of smaller defects and particles on the wafer. Therefore, higher power and shorter wavelength ultraviolet (UV) lasers for wafer inspection are needed. Because the defect or particle size is reduced, the fraction of the light reflected or scattered by that defect or particle is also typically reduced. As a result, an improved signal-to-noise ratio may be needed to detect smaller defects and particles. If a brighter light source is used to illuminate the defect or particle, then more photons will be scattered or reflected and the signal-to-noise ratio can be improved if other noise sources are controlled. Using shorter wavelengths can further improve the sensitivity to smaller defects because the fraction of light scattered by a particle smaller than the wavelength of light increases as the wavelength decreases.

Harmonic generation in nonlinear optical crystal materials is a technique to generate high power laser radiation in the visible, UV, and DUV spectral regions. Some inspection tools for wafers and reticle inspection used in the semiconductor industry rely on DUV radiation. Frequency doubling (i.e., second harmonic generation or "SHG") is one commonly used form of harmonic generation. In order to achieve high conversion efficiencies, the phase velocities of the fundamental and the second harmonic waves may be identical (i.e., their phases are matched). This can be achieved in birefringent nonlinear crystals by adjusting the angle between the beam propagation direction and the optical axis "Z" of the crystal, as well as the temperature of the crystal. This phase matching condition can only be met when a suitable combination of phase matching angle and phase matching temperature is chosen. The required angle and temperature tolerances are typically in the range of tens of microradians and 0.1 K, respectively. Therefore, the nonlinear crystal is mounted on a base or inside an oven cell with a sufficiently accurate angle alignment and a sufficiently accurate temperature control.

Nonlinear crystals, commonly used for the generation of UV and DUV wavelengths include, but are not limited to, lithiumtriborate (LBO), beta-bariumborate (BBO), lithiumiodate, and cesium-lithiumborate (CLBO). With the exception of BBO, all of the above mentioned crystals are highly hygroscopic. Excess humidity can induce surface degradation in the case of LBO and CLBO. Excess humidity can destroy the entire crystal structure in the case of CLBO. Therefore, such crystals have to be either stored and operated in a sealed dry enclosure, or purged with a dry purge gas. Typical purge gases include, but are not limited to, clean dry air (CDA), argon, or nitrogen. One operating condition is to position the nonlinear crystal in a purged enclosure that is sealed except for the purge gas inlet and outlet. In addition to the dry purge, an elevated phase matching temperature, typically in the range of 50° C. to 200° C., is frequently chosen to provide additional protection against moisture.

When purging a heated oven cell, purge gas enters the oven cell at or near room temperature and mixes with the hot gas inside the chamber. The mixing of purge gases having different temperatures results in pointing variations and beam distortions of laser beams transmitted though the oven cell. If the nonlinear crystal is located inside a sealed and purged laser head with a typical length between 0.5 m and 1 m, the purge inlet can be located relatively far away from the crystal oven to minimize beam distortions and pointing variation. However, this may not be possible if a small, field replaceable, purged oven cell for the nonlinear crystal is used. In this case, the purged volume is small and the purge inlet is located close to the nonlinear crystal, which, as a consequence, is close to the laser beam transmitted through it. If CDA is used as a purge gas at an oven temperature of 100° C., the refractive index difference between the incoming air at room temperature and the air inside the oven at 100° C. is $6*10^{-6}$ at a wavelength of 300 nm. For an incoming air flow with 5 mm width along the beam propagation direction and a temperature gradient of 30° C./cm in the lateral direction, the result is a beam deflection of more than 10 micro-radians. A beam pointing variation on this order of magnitude can negatively impact applications that are sensitive to beam position and beam pointing, such as the generation of a flat-top beam profile using a diffractive optical element (DOE). If a turbulent purge-gas flow develops, temperature gradients are expected to be larger than is the example and, in addition, to show strong variations over time.

Therefore, what is needed is improved devices and operating techniques for nonlinear crystals or optical components, which minimizes the detrimental effects of a cold or room temperature purge gas flow entering a heated crystal enclosure.

BRIEF SUMMARY OF THE DISCLOSURE

In a first embodiment, an oven enclosure is provided. The oven enclosure comprises a plurality of walls defining an oven chamber; a cartridge disposed in the walls; a purge gas inlet disposed in one of the walls; two windows disposed in the walls; and a purge gas outlet disposed in one of the walls. The cartridge includes: a cartridge block; a mount disposed on a first surface of the cartridge block; a gas pathway disposed on the cartridge block; and a heater disposed on the cartridge block. The mount is configured to hold an optical component. The purge gas inlet is configured to be in fluid communication with the gas pathway. The windows are positioned such that a laser beam enters through one of the windows, passes through the optical component, and exits through another of the windows. The purge gas outlet is configured to be in fluid communication with the oven chamber.

The gas pathway can include tubing wound around a surface of the cartridge block. The tubing can be fabricated of a metal.

The cartridge block can include a surface that defines a groove. The groove may be spirally arranged around the surface of the cartridge block.

The oven enclosure can further comprise an optical component disposed on the mount. The optical component may be a non-linear optical crystal.

The mount may be spring-loaded. In an instance, the mount has a spring force from 10 to 100 times a weight of the optical component.

The oven enclosure can further comprise a purge gas source. The purge gas source can contain at least one of air, nitrogen, or argon.

The oven enclosure can further comprise a filter disposed in fluid communication with the purge gas inlet. The filter can be configured to remove at least one of volatile organic compounds, humidity, or particles.

The oven enclosure can further comprise a seal disposed between the cartridge and one of the walls.

The gas pathway may have a helical pattern around the cartridge block.

The heater may be disposed at least partly inside the cartridge block.

The windows can include an anti-reflection coating for light having at least one wavelength. The windows also can be configured to be tilted at Brewster's angle relative to a beam propagation direction of the laser beam thereby minimizing reflection of polarized laser radiation.

In a second embodiment, a cartridge is provided. The cartridge comprises a cartridge block; a mount disposed on a first surface of the cartridge block; a gas pathway disposed on the cartridge block; and a heater disposed on the cartridge block. The mount is configured to hold an optical component.

The gas pathway can include tubing wound around a surface of the cartridge block. The tubing can be fabricated of a metal.

The cartridge block can include a surface that defines a groove. The groove may be spirally arranged around the surface of the cartridge block.

The cartridge can further comprise an optical component disposed on the mount. The optical component may be a non-linear optical crystal.

The mount may be spring-loaded. In an instance, the mount has a spring force from 10 to 100 times a weight of the optical component.

The gas pathway may have a helical pattern around the cartridge block.

The heater may be disposed at least partly inside the cartridge block.

In a third embodiment, a method is provided. The method comprises: providing an oven enclosure; disposing a cartridge in the oven enclosure; biasing the heater; flowing a purge gas through the gas pathway into the oven enclosure; and directing a laser beam through the oven enclosure. The cartridge includes: a cartridge block; a mount disposed on a first surface of the cartridge block; a gas pathway disposed on the cartridge block; and a heater disposed on the cartridge block. The mount is configured to hold an optical component. The heater is configured to increase a temperature of the purge gas as the purge gas flows through the gas pathway.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

The cartridge and oven enclosure embodiments disclosed herein address the drawbacks of existing purged oven cell designs for hygroscopic nonlinear optical crystals. The embodiments disclosed herein include a pre-heating feature for the incoming purge gas before it enters the space around an optical component (e.g., a nonlinear optical crystal) in an oven cell, which can be kept in a clean and dry environment at an elevated temperature during operation. The incoming purge gas can be pre-heated as it travels along a path around a cartridge, which can include a heater. The path may be helical or other patterns. The heater may be the primary heater used to heat the oven cell. Pre-heating the purge gas can minimize the beam distortions and beam pointing variations of a laser beam transmitted through the oven cell, which can be introduced by the mixing of gases with different temperatures and, thus, different refractive indices. Furthermore, pre-heating the purge gas can reduce the cooling effect of the purge gas on the facets of the optical component.

Figure 1:
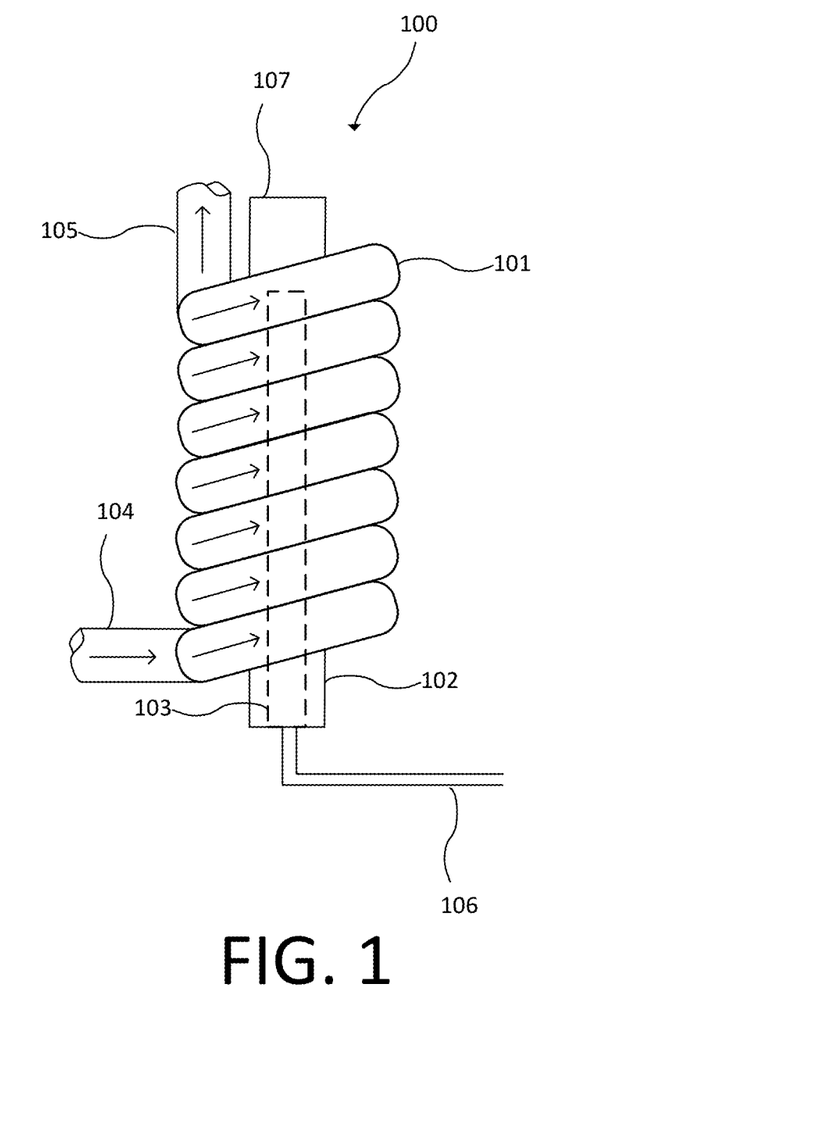
FIG. 1 is a view of an embodiment of a cartridge in accordance with the present disclosure.

FIG. 1 is a view of an embodiment of a cartridge 100. The cartridge 100 includes a cartridge block 102 and a gas pathway 101 disposed on the cartridge block 102. The cartridge block 102 may be a cylinder or other shapes. The cartridge block 102 may be fabricated of stainless steel, copper, a copper alloy, aluminum, an aluminum alloy, nickel, a nickel alloy, a ceramic, a combination thereof, or other materials.

The gas pathway 101 can wind around a circumferential or exterior surface of the cartridge block 102. The gas pathway 101 may be tubing, such as metal tubing. A heater 103 (shown with dotted lines) is disposed on the cartridge block 102. For example, the heater 103 can be disposed at least partly inside the cartridge bock 102, such as in a center of the cartridge block 102. In an instance, the heater 103 is fully disposed inside the cartridge block 102. The heater 103 also can be on the surface of the cartridge block 102 or at other positions on or in the cartridge block 102. An optical component, such as a non-linear optical crystal, can be connected to a first surface 107 of the cartridge block 102.

While the gas pathway 101 is shown as tubing wound around a surface of the cartridge block 102, other types of gas pathways 101 are possible. The gas pathway 101 can include machined structures, metal piping, or other components positioned around or in the cartridge block 102. For example, the cartridge block can include a surface with a groove that is spirally arranged around the surface of the cartridge block 102.

The gas pathway 101 includes both an inlet 104 and outlet 105. The incoming gas from the inlet 104 used to purge an enclosed crystal oven travels around the cartridge block 102 and heater 103 (as indicated by the arrows in FIG. 1) to the outlet 105. The gas that passes through the gas pathway 101 can be pre-heated as it enters an oven chamber, which can minimize beam distortions and pointing variations induced by temperature gradients in the mixing gas.

The heater 103 may be an electrical heater, such as a cartridge heater or another type of resistive heater. Other heater designs are possible. Electrical connectors 106 are attached to the heater 103.

Figure 2:
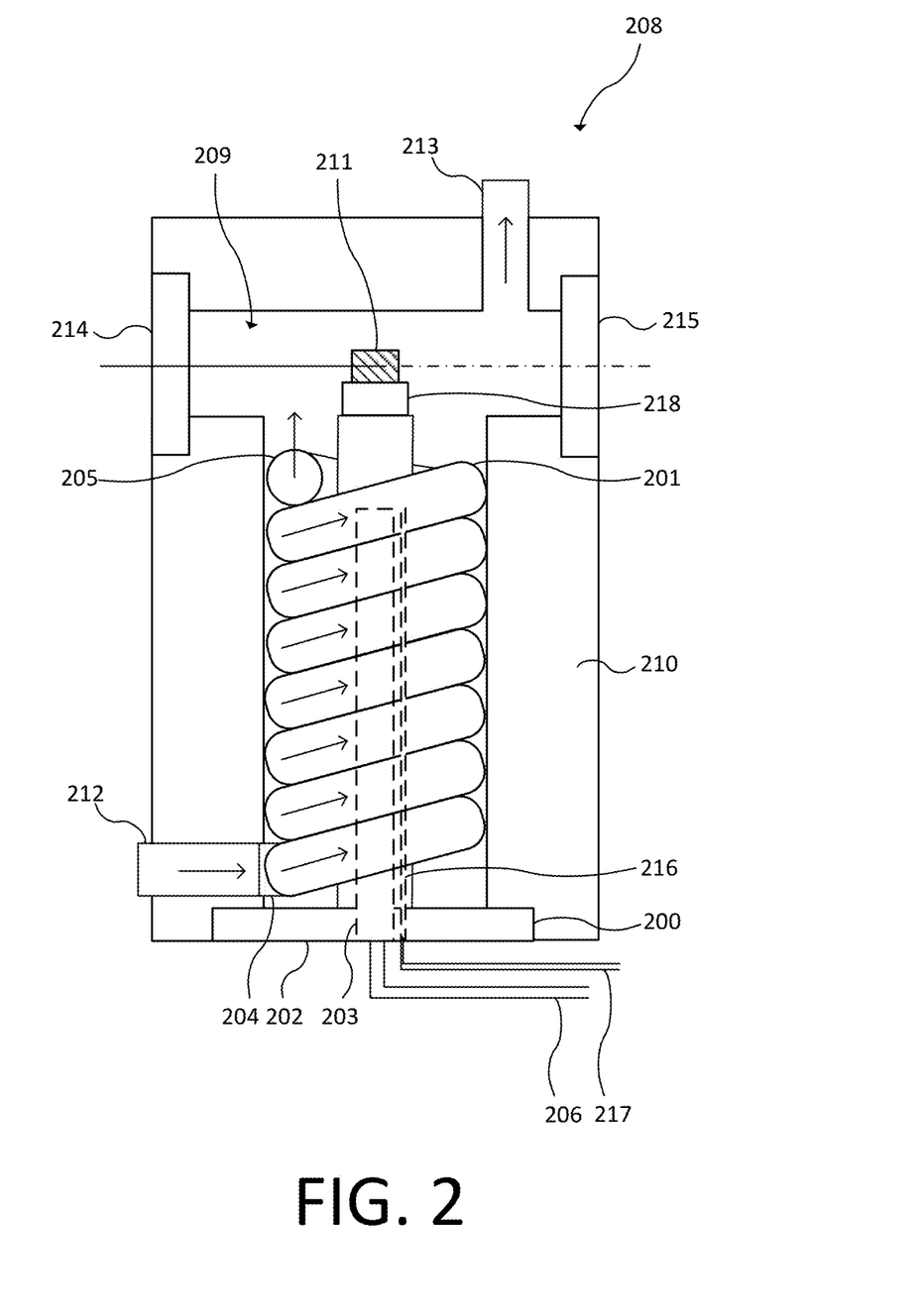
FIG. 2 is a view of an embodiment of an oven enclosure in accordance with the present disclosure.

FIG. 2 is a view of an embodiment of an oven enclosure 208. The oven enclosure 208 has walls 210 that define an oven chamber 209. A cartridge 200 is positioned on or against the walls 210 of the oven enclosure 208. The cartridge 200 may be in the cavity of the oven chamber 209 formed by the walls 210. The cartridge 200 may be similar to the cartridge 100 of FIG. 1 and can include a cartridge block 202. The cartridge 200 can be inserted into a cavity formed by the walls 210 of the oven enclosure 208 such that the cartridge 200 fills a gap formed by the walls 210.

A non-linear optical crystal 211 (shown with hatching) is positioned on a first surface of the cartridge block 202. The non-linear optical crystal 211 is in the oven chamber 209. The non-linear crystal 211 may be LBO, BBO, lithiumiodate, CLBO, or other materials. Other optical components besides the non-linear crystal 211 also can be positioned on a first surface of the cartridge block 202.

A gas pathway 201 is disposed around the cartridge block 202. The gas pathway 201 may be a pipe or tube. For example, the gas pathway 201 may include a stainless steel pipe which is wound around the exterior surface of the cartridge block 202.

The gas pathway 201 can include both an inlet 204 and outlet 205. The outlet 205 emits purge gas to the oven chamber 209. A purge gas inlet 212 is positioned in or attached to one of the walls 210 of the oven enclosure 208. The purge gas inlet 212 is configured to be in fluid communication with the gas pathway 201, such as with the inlet 204. The connection between the purge gas inlet 212 and the gas pathway 201 can include a seal or may be configured to have a tolerance configured to provide gas flow. A purge gas outlet 213 is in or attached to one of the walls 210 of the oven enclosure 208. The purge gas outlet 213 is configured to be in fluid communication with the oven chamber 209 and may be near one of the windows 214, 215 to provide a cleaning action.

A heater 203 is disposed in the cartridge block 202. Electrical connectors 206 are attached to the heater 203. The heater 203 pre-heats the purge gas passing through the cartridge block 202. The purge gas is pre-heated as it travels along a gas pathway 201 as indicated by arrows. The gas pathway 201 passes the heater 203 one or more times. A gas pathway 201 that is helical-shaped can be a compact and efficient way to pre-heat the purge gas, but other patterns are possible. The gas pathway 201 can wind around the heater 203 before it leads to the outlet 205 in or in fluid communication with the oven chamber 209, which can contain one or more optical components that may require accurate temperature control. For example, the oven chamber 209 has the non-linear optical crystal 211. Pre-heating the purge gas can minimize gradients and temporal variations in purge gas temperature, density, and refractive index, which can reduce spatial beam distortions and/or position and pointing variations of laser beams transmitted through the oven cell.

There are two windows 214, 215 disposed in the walls 210 around the oven chamber 209. The windows 214, 215 are positioned such that a laser beam can enter through one of the windows 214, pass through the non-linear optical crystal 211 or other optical component, and exit through another of the windows 215. An anti-reflection coating on the windows 214, 215 may be configured for light having at least one wavelength. For example, the windows 214, 215 may be anti-reflection coated at the fundamental and/or the harmonic wavelength. The windows 214, 215 also may be tilted at Brewster's angle relative to the beam propagation direction to minimize the reflection of polarized laser beams on the window facets.

While the non-linear optical crystal 211 is disclosed, additional optical components or different optical components also can be used. These optical components, including the non-linear optical crystal 211, may be part of a laser or a nonlinear optical wavelength converter. The optical components may include, but are not limited to, one or more non-linear crystals, laser-active solid state materials, or passive optical components.

In an example, a length of the gas pathway 201 can be optimized so that the temperature of the purge gas entering the oven chamber 209 is within a desired temperature range. For example, the temperature of the purge gas may be within $\Delta T \leq 5$ K of the heater 203 temperature. A purge gas outside the desired temperature range may cause turbulence in the oven chamber 209 and, thus, may cause diffraction, beam shape distortions, or beam pointing variations.

The heater 203 that pre-heats the purge gas may be the primary heating mechanism of the oven cell 209 or an auxiliary heating mechanism used for purge gas pre-heating. Depending on an allowable tolerance of the purge gas temperature, the heater 203 or cartridge block 202 may include a temperature sensor 216 (shown in dotted lines) connected to electrical connectors 217. The heater 203 may use an active temperature control loop, which can use measurements from the temperature sensor 216. The temperature sensor 216 may be, for example, a thermistor, a thermocouple, or a resistance temperature detector (RTD) temperature sensor (e.g., a platinum RTD temperature sensor).

Alternatively, the heater 203 may be operated at a constant electrical current.

Figure 3:
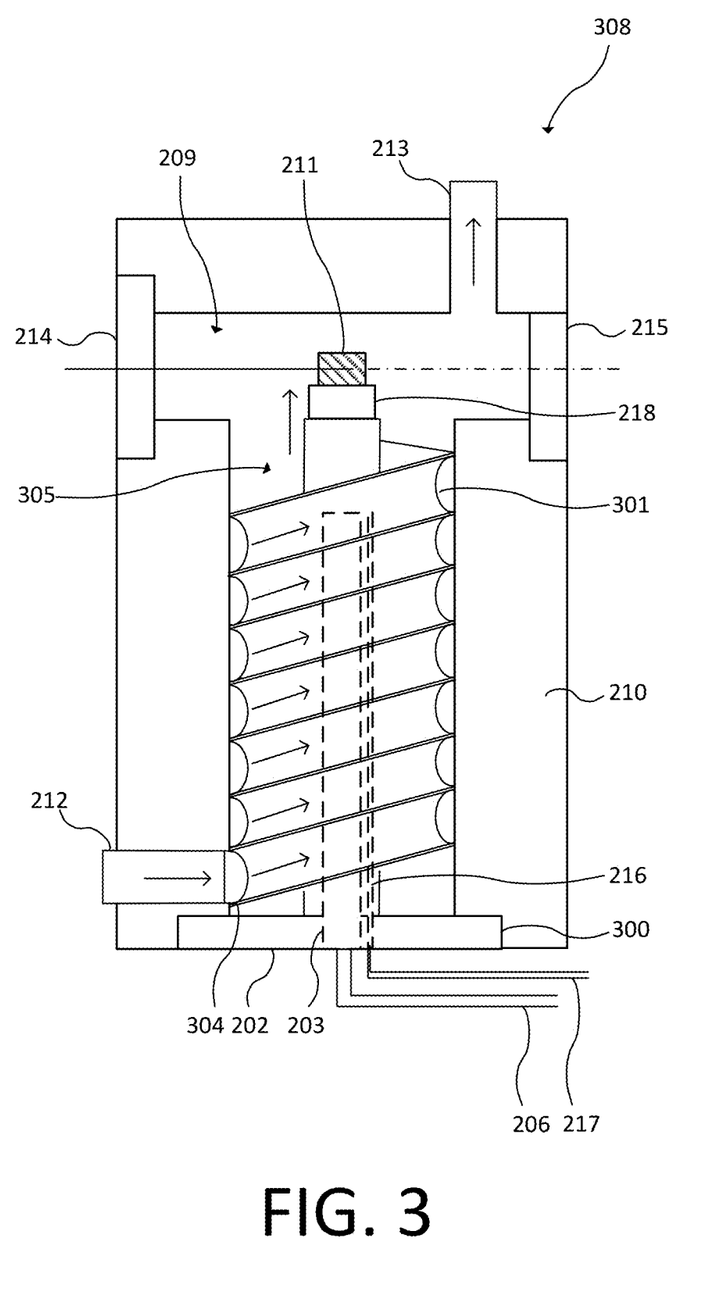
FIG. 3 is a view of another embodiment of an oven enclosure in accordance with the present disclosure.

FIG. 3 is a view of another embodiment of an oven enclosure 308. The gas pathway 301 includes features machined into the cartridge block 202. For example, the surface of the cartridge block 202 can include a groove that is arranged around the surface of the cartridge block 202. The surface of the cartridge block 202 that forms the groove and the walls 210 form the gas pathway 301 around the cartridge 300. The groove of the gas pathway 301 may be in a spiral or helical pattern or may be other patterns. The tolerance of the shape of the gas pathway 301 and/or the position proximate to the walls 210 can enable the purge gas to flow through the gas pathway 301 with a minimized amount of leakage. In an instance, purge gas leaks upward from a gap between the gas pathway 301 and/or the position proximate to the walls 210 into the oven chamber 209. Any effect of leaked purge gas can be compensated for.

The cartridge 200 and cartridge 300 both include a non-linear optical crystal 211 and/or one or more other optical components. The cartridge 200 and cartridge 300 include a mount 218 for the non-linear optical crystal 211 and/or one or more other optical components. The mount 218 may be spring-loaded or may use other mechanisms. In a mount 218 that is spring-loaded, the holding force of the spring or springs may be selected so that it equals a multiple of the crystal weight, which can securely hold the crystal for the shock level required for safe shipment (e.g., up to 20 g). Small optical components, such as non-linear crystals, typically only weigh a few grams, so the mount 218 can be configured to avoid excessive strain to the optical component that may introduce strain birefringence or cause damage to the optical component (e.g., crack formation). Spring loading also can compensate for a coefficient of thermal expansion mismatch between the optical component and the mount 218 when the oven cell 209 is temperature cycled from room temperature to its operating temperature. In an example, the mount has a spring force from 10 to 100 times a weight of the optical component (including all values to the 0.1 and ranges therebetween), which can securely hold a non-linear crystal while compensating for coefficient of thermal expansion mismatch.

Mounting the optical component to the cartridge 200 or cartridge 300 with the mount 218 provides advantages. First, it allows a fast and simple cartridge-based replacement of highly sensitive optical components, such as a non-linear crystal, which can minimize the handling risk. Second, mounting the optical component on the cartridge 200 or cartridge 300 can optimize the thermal contact between heater 203 and temperature sensor 216 and between the heater 203 and the optical component. Thus, temperature control accuracy and stability can be improved. In this configuration the heater 203 used to pre-heat the purge gas may be the heat source (e.g., a primary heat source) of the oven enclosure, which reduces complexity of the temperature control and the cost of the oven enclosure.

In the embodiments disclosed herein, the purge gas may enter the gas pathway at room temperature. The purge gas may exit the gas pathway in the area proximate the optical element at a temperature from 50° C. to 200° C., including all ranges and values to the 0.1° C. therebetween.

Figure 4:
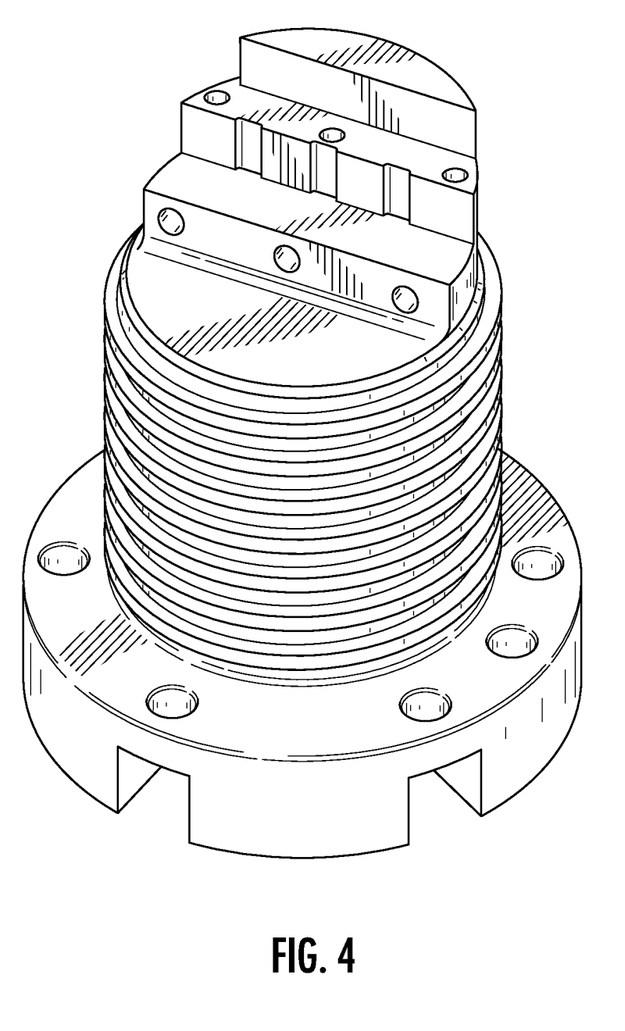
FIG. 4 is a view of an embodiment of a cartridge for use in the oven enclosure of FIG. 3.

FIG. 4 is a view of an embodiment of a cartridge for use in the oven enclosure of FIG. 3. As seen in FIG. 4, grooves are formed in the cartridge block.

While a single tube or groove is disclosed in FIGS. 2-4, multiple gas pathways in a single cartridge are possible. For example, two gas pathways can be used if there are two purge gas inlets, such as for two different purge gases.

An alignment pin or other alignment mechanism can be used to ensure the cartridge block is aligned to the oven chamber. This can provide a desired connection between the purge gas inlet and the gas pathway and a desired positioning of the non-linear optical crystal or other optical component.

The height of the heater relative to the height of the cartridge block can vary. While the height of the heater is illustrated as being approximately the same height as the distance the gas pathway extends up the cartridge block, the height of the heater can be less than or more than this height. The cartridge block can spread heat from the heater to all regions of the gas pathway even if the heater is less than the height of the cartridge block.

The number of coils around the cartridge block can vary. This may depend on, for example, the desired temperature of the purge gas when it enters the area proximate the optical element relative to the temperature of the purge gas supplied to the gas pathway.

The size of the gas pathway can vary. For example, the diameter or width of the gas pathway may be configured to prevent turbulent flow of the purge gas. The diameter or width of the gas pathway also may be configured to provide laminar flow of the purge gas when it enters the area proximate the optical element.

The shape of the cartridge block can vary. While illustrated with part having a circular cross-section, the cartridge block can have a square cross-section, a triangular cross-section, a hexagonal cross-section, an elliptical cross-section, or a cross-section of some other shape.

The gas pathway also can be inside the cartridge block or the cartridge block can include an additional fitting (e.g., a ring or outer wall) between the gas pathway and the walls of the oven chamber. This can prevent damage to the gas pathway during insertion of the cartridge.

Embodiments of the cartridge disclosed herein may be removable from the oven enclosure.

An interface between the cartridge and the oven enclosure may be sealed. The seal may include one or more o-rings, metal c-rings containing a helicoil spring (such as those manufactured by Technetics Helicoflex, Technetics Group, Columbia, S.C.), compression seals (such as those manufactured by Agilent Conflat, Agilent Technologies, Santa Clara, Calif.), soft metal seals, soldered interfaces, welded interfaces, or other sealing mechanisms. A seal at an interface between the cartridge and the oven enclosure can keep purge gas in the oven enclosure and can help maintain the purge gas at the desired temperature, the desired level of dryness, and/or the desired level of cleanliness.

The purge gas can be, for example, at least one of air (e.g., CDA), nitrogen, or argon. Other purge gases, such as other noble gases or inert gases, also can be used.

Figure 5:
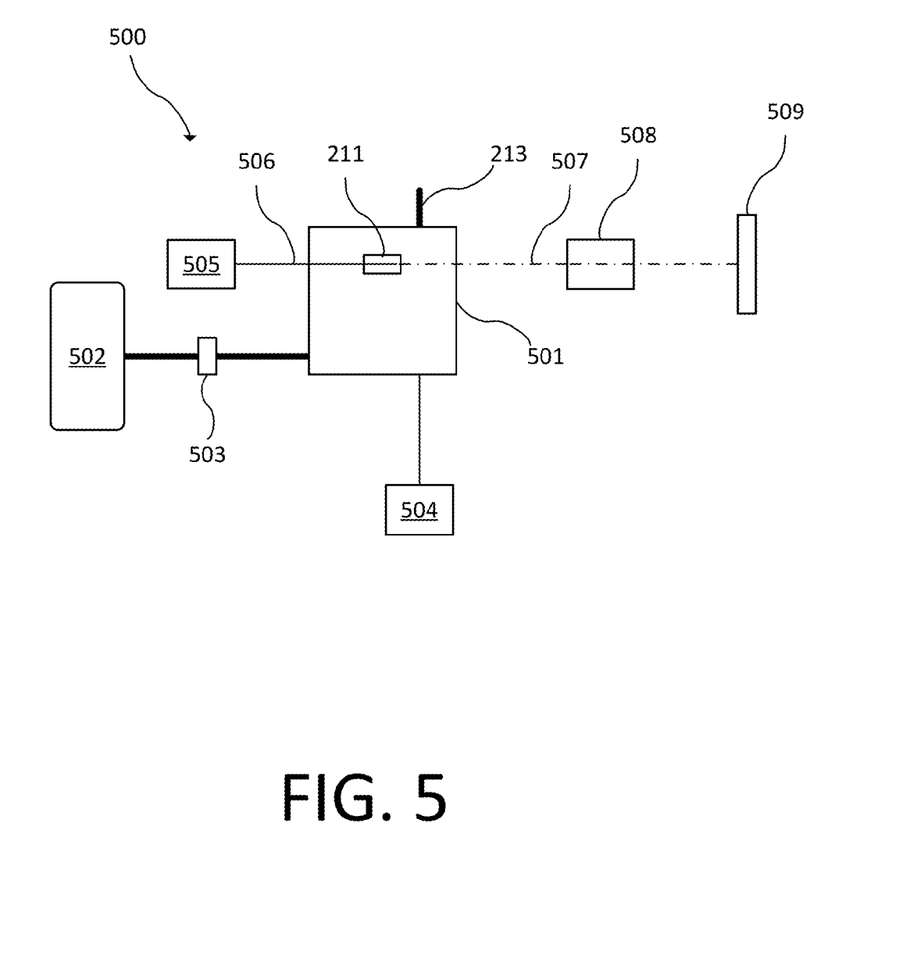
FIG. 5 is a block diagram of a system to be used with the oven enclosures.

FIG. 5 is a block diagram of a system 500 to be used with the oven enclosures disclosed herein. The system 500 includes an oven enclosure 501 with a non-linear crystal 211 and/or other optical component. The oven enclosure 501 may be the oven enclosure 208 of FIG. 2 or the oven enclosure 308 of FIG. 3. The oven enclosure 501 includes a cartridge, such as the cartridge 100, 200, or 300. The oven enclosure also includes a purge gas outlet 213.

The oven enclosure 501 is fluidically connected with a purge gas source 502 and an optional filter 503. The filter 503 is positioned between the oven enclosure 501 and the purge gas source 502. The filter 503 can remove or reduce at least one chemical contaminant from the purge gas, such as volatile organic contaminants, humidity, or particles.

The oven enclosure 501 or a heater and/or temperature sensor of the cartridge in the oven enclosure 501 is connected with a controller 504. The controller 504 can be configured to control the temperature of the purge gas in the oven enclosure 501. The controller 504 also can control a flow rate of the purge gas through the gas pathway.

The controller 504 can include a processor, an electronic data storage unit in electronic communication with the processor, and a communication port in electronic communication with the processor. It is to be appreciated that the controller 504 may be implemented in practice by any combination of hardware, software, and firmware. Also, its functions as described herein may be performed by one unit, or divided up among different components, each of which may be implemented in turn by any combination of hardware, software, and firmware. Program code or instructions for the controller 504 to implement the various methods and functions described herein may be stored in controller readable storage media, such as a memory in the electronic data storage unit, within the controller 504, external to the controller 504, or combinations thereof.

The controller 504 may be coupled to the components of the system 500 in any suitable manner (e.g., via one or more transmission media, which may include "wired" and/or "wireless" transmission media) such that the controller 504 can receive the output generated by the system 500, such as output from the temperature sensor. The controller 504 may be configured to perform a number of functions using the output. For instance, the controller 504 may be configured to increase or decrease a temperature of a heater that adjusts a temperature of the purge gas in the oven enclosure 501.

The controller 504, other system(s), or other subsystem(s) described herein may take various forms, including a microcontroller, personal computer system, image computer, mainframe computer system, workstation, network appliance, internet appliance, or other device. In general, the term "controller" may be broadly defined to encompass any device having one or more processors that execute instructions from a memory medium. The subsystem(s) or system(s) also may include any suitable processor known in the art, such as a parallel processor. In addition, the subsystem(s) or system(s) may include a platform with high speed processing and software, either as a standalone or a networked tool.

A light source 505 is configured to generate a beam of light, such as a laser beam. The fundamental beam 506 is directed at the non-linear crystal 211 and/or other optical components in the oven enclosure 501. One or more additional beam shaping optics may be positioned between the light source 505 and the oven enclosure 501. For example, beam shaping optics may be used to focus the fundamental beam 506.

A second harmonic beam 507 is produced when the fundamental beam 506 passes through, for example, the non-linear crystal 211. One or more beam shaping optics 508 can be positioned between the oven enclosure 501 and a wafer 509. A harmonic separation block or one or more other optical components also may be positioned between the oven enclosure 501 and the wafer 509.

The second harmonic beam 507 is used to inspect or image the wafer 509. For example, the wafer 509 can be inspected for surface anomalies using the second harmonic beam 507.

As used herein, the term "wafer" generally refers to substrates formed of a semiconductor or non-semiconductor material. Examples of such a semiconductor or non-semiconductor material include, but are not limited to, monocrystalline silicon, gallium nitride, gallium arsenide, indium phosphide, sapphire, and glass. Such substrates may be commonly found and/or processed in semiconductor fabrication facilities.

A wafer may include one or more layers formed upon a substrate. For example, such layers may include, but are not limited to, a photoresist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

Figure 6:
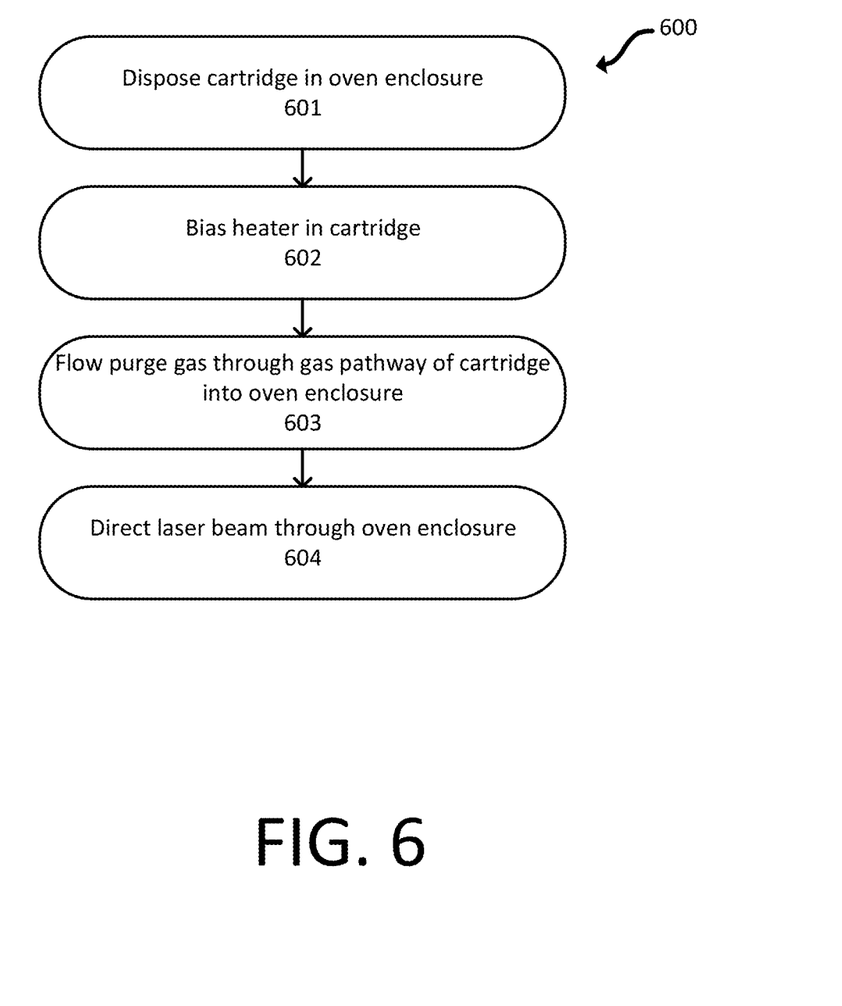
FIG. 6 is a flowchart of a method in accordance with the present disclosure.

FIG. 6 is a flowchart of a method in accordance with the present disclosure. In the method 600, an oven enclosure is provided. A cartridge is disposed 601 in the oven enclosure. The cartridge can include a cartridge block; a non-linear optical crystal or other optical component disposed on a first surface of the cartridge block; a gas pathway disposed around the cartridge block; and a heater disposed in a center of the cartridge block.

The heater is biased 602 and a purge gas flows 603 through the gas pathway. In another instance, the purge gas flows 603 through the gas pathway prior biasing 602 the heater. In yet another instance, the heater is biased 602 and a purge gas begins flowing 603 through the gas pathway simultaneously. The heater is configured to increase a temperature of the purge gas as the purge gas flows through the gas pathway. The purge gas can be, for example, at least one of air (e.g., CDA), nitrogen, or argon.

A laser beam is directed 604 through the oven enclosure. In an instance, the laser beam is directed 604 through the oven enclosure after the purge gas is at a particular temperature. In another instance, the laser beam is directed 604 through the oven enclosure before the purge gas is at a particular temperature.

At least one chemical contaminant, such as volatile organic contaminants, humidity, or particles, can be filtered from the purge gas prior to the purge gas flowing through the gas pathway.

Each of the steps of the method may be performed as described further herein. The method also may include any other step(s) that can be performed by the controller and/or computer subsystem(s) or system(s) described herein. The steps can be performed by one or more computer systems, which may be configured according to any of the embodiments described herein. In addition, the methods described above may be performed by any of the system embodiments described herein.

The embodiments disclosed herein address at least two problems typically encountered with purged ovens and oven enclosures for optical components, such as nonlinear optical crystals. First, pre-heating the purge gas can minimize temperature gradients inside the oven cell and, thus, refractive index gradients that may be caused by the flow of cold purge gas around the heated optical component. The embodiments disclosed herein can minimize distortions and pointing variations of a laser beam transmitted through the oven cell, which may be caused by such refractive index gradients in the purge gas.

Pre-heating the purge gas also can minimize cooling of the optics facets by the impinging cold purge gas. If the optical component is a nonlinear optical crystal, the resulting reduction of temperature gradients inside the crystal along the beam propagation direction can be advantageous. For example, reduction of temperature gradients may improve the nonlinear conversion efficiency and may minimize the negative impact of temperature gradients on the spatial beam profile of the generated second harmonic beam, particularly in the critical direction of phase matching.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An oven enclosure comprising:
   a plurality of walls defining an oven chamber; and
   a cartridge disposed in the walls, wherein the cartridge includes:
      a cartridge block;
      a mount disposed on a first surface of the cartridge block, wherein the mount is configured to hold an optical component;
      a gas pathway disposed on the cartridge block, wherein the gas pathway includes tubing wound around a surface of the cartridge block; and
      a heater disposed on the cartridge block;
   a purge gas inlet disposed in one of the walls, wherein the purge gas inlet is configured to be in fluid communication with the gas pathway;
   two windows disposed in the walls, wherein the windows are positioned such that a laser beam enters through one of the windows, passes through the optical component, and exits through another of the windows; and
   a purge gas outlet disposed in one of the walls, wherein the purge gas outlet is configured to be in fluid communication with the oven chamber.

2. The oven enclosure of claim 1, wherein the tubing is fabricated of a metal.

3. The oven enclosure of claim 1, further comprising an optical component disposed on the mount, wherein the optical component is a non-linear optical crystal.

4. The oven enclosure of claim 1, wherein the mount is spring-loaded.

5. The oven enclosure of claim 4, wherein the mount has a spring force from 10 to 100 times a weight of the optical component.

6. The oven enclosure of claim 1, further comprising a purge gas source, wherein the purge gas source contains at least one of air, nitrogen, or argon.

7. The oven enclosure of claim 1, further comprising a filter disposed in fluid communication with the purge gas inlet, wherein the filter is configured to remove at least one of volatile organic compounds, humidity, or particles.

8. The oven enclosure of claim 1, further comprising a seal disposed between the cartridge and one of the walls.

9. The oven enclosure of claim 1, wherein the gas pathway has a helical pattern around the cartridge block.

10. The oven enclosure of claim 1, wherein the heater is disposed at least partly inside the cartridge block.

11. The oven enclosure of claim 1, wherein the windows include an anti-reflection coating for light having one or multiple wavelengths.

12. The oven enclosure of claim 1, wherein the windows are configured to be tilted at Brewster's angle relative to a beam propagation direction of the laser beam thereby minimizing reflection of polarized laser radiation.

13. A method comprising:
   providing an oven enclosure;
   disposing a cartridge in the oven enclosure, wherein the cartridge includes:
      a cartridge block;
      a mount disposed on a first surface of the cartridge block, wherein the mount is configured to hold an optical component;
      a gas pathway disposed on the cartridge block, wherein the gas pathway includes tubing wound around a surface of the cartridge block; and
      a heater disposed on the cartridge block;
   biasing the heater;
   flowing a purge gas through the gas pathway into the oven enclosure, wherein the heater is configured to increase a temperature of the purge gas as the purge gas flows through the gas pathway; and
   directing a laser beam through the oven enclosure.

\* \* \* \* \*